(12) United States Patent
Schwarz et al.

(10) Patent No.: US 6,750,375 B2
(45) Date of Patent: Jun. 15, 2004

(54) TRANSGENIC MOUSE COMPRISING A DISRUPTION IN AN RGS9 GENE

(75) Inventors: Johannes Schwarz, Leipzig (DE); Ching-Kang Chen, Salt Lake City, UT (US); Melvin I. Simon, San Marino, CA (US); Henry Lester, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 67 days.

(21) Appl. No.: 09/999,746

(22) Filed: Oct. 23, 2001

(65) Prior Publication Data

US 2002/0095693 A1 Jul. 18, 2002

Related U.S. Application Data

(60) Provisional application No. 60/242,656, filed on Oct. 23, 2000.

(51) Int. Cl.[7] .................... C12N 15/00; G01N 33/00
(52) U.S. Cl. ................. 800/18; 800/3; 800/25
(58) Field of Search ................. 800/3, 14, 18

(56) References Cited

PUBLICATIONS

Gold, Stephen J. et al. "Regulators of G–Protein Signaling (RGS) Proteins: Region–Specific Expression of Nine Subtypes in Rat Brain", *Journal of Neuroscience*, vol. 17, No. 20, pp. 8024–8037, Oct. 1997.

He, Wei et al., "RGS9, a GTPase Accelerator for Phototransduction", *Neuron*, vol. 20, pp. 95–102, Jan. 1998.

Burchett, Scott A. et al, "Regulators of G Protein Signaling: Rapid Changes in MRNA Abundance in Response to Amphetamine", *Journal of Neurochemistry*, pp. 2216–2219, 1998.

Thomas, Elizabeth A. et al., RGS9: A Regulator of G–Protein Signalling With Specific Expression in Rat and Mouse Striatum, *Journal of Neuroscience Research*, vol. 52, pp. 118–124, 1998.

Rahman, Z. et al., "Characterization of the RGS9 Gene: Identification of Multiple Splice Variants that Show Region–Specific Expression Patterns in Brain", *Society for Neuroscience*, vol. 24, p. 1361, abstract 143.4, 1998.

Rahman, A. et al., "Cloning and Characterization of RGS9–2: A Striatal–Enriched Alternatively Spliced Product of the RGS9 Gene", *The Journal of Neuroscience*, vol. 19, No. 6, pp. 2016–2026, Mar. 1999.

Zhang, K. et al., "Structure, alternative splicing, and expression of the human RGS9 gene", *Gene*, vol. 240, pp. 23–34, 1999.

Chen, C–K. et al, "Slowed Recovery of Rod Photoresponse in Mice Lacking the GTPase Accelerating Protein RGS9–1", *Nature*, vol. 403, pp. 557–560, Feb. 2000.

Kovoor, A. et al., "Co–expression of Gβ5 Enhances the Function of Two Gγ Sunbunit–like Domain–contaiing Regulators of G Protein Signaling Proteins", *The Journal of Biological Chemistry*, vol. 275, No. 5, pp. 3397–3402, Feb. 2000.

Schwarz, J. et al, "RGS9 Deficiency Increases Dopamine D2 Receptor Mediated Locomotion", *Society for Neuroscience*, vol. 26, p. 1938, abstract 624.14, 2000.

Lyubarsky, Al. L. et al, "RGS(–/–Mice Have Profoundly Slowed Recovery of Cone Responses After Intense Flashes", *Society for Neuroscience*, vol. 26, p. 1192, abstract 446.4, 2000.

De Vries, Luc et al, "The Regulator of G Protein Signaling Family", *Annu. Rev. Pharmacol. Toxicol.*, vol. 40, pp. 235–271, 2000.

*Primary Examiner*—Deborah Crouch
(74) *Attorney, Agent, or Firm*—Gray Cary Ware & Freidenrich, LLP

(57) ABSTRACT

The invention relates to an animal model for studying behavior related to RGS9 and RGS9 modulated dopamine D2-mediated behavior. The invention provides transgenic non-human animals in which RGS9 expression is disrupted, methods of using such animals, and methods of modulating dopamine D2-mediated behavior.

10 Claims, 5 Drawing Sheets

A

B

C

D

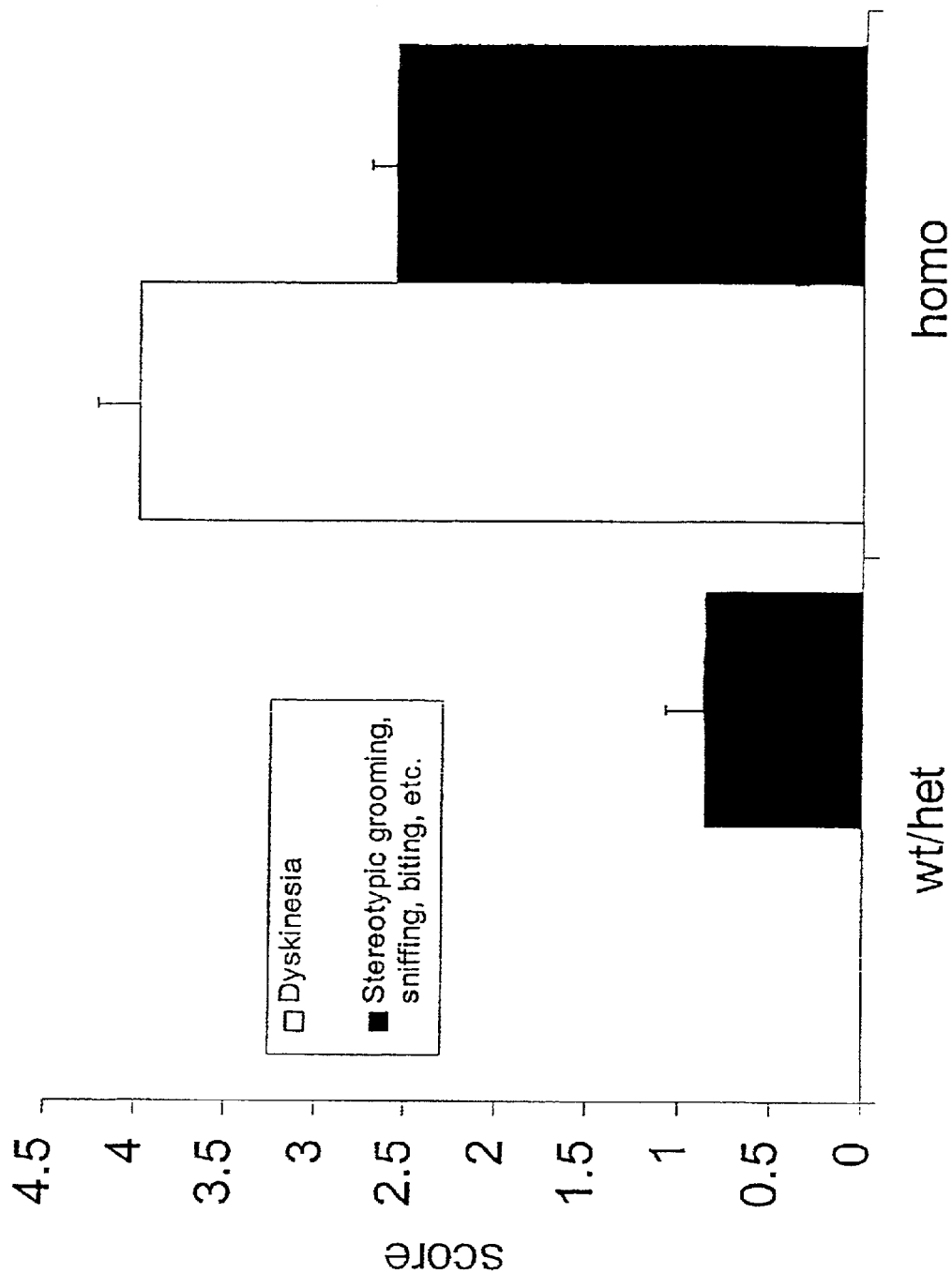

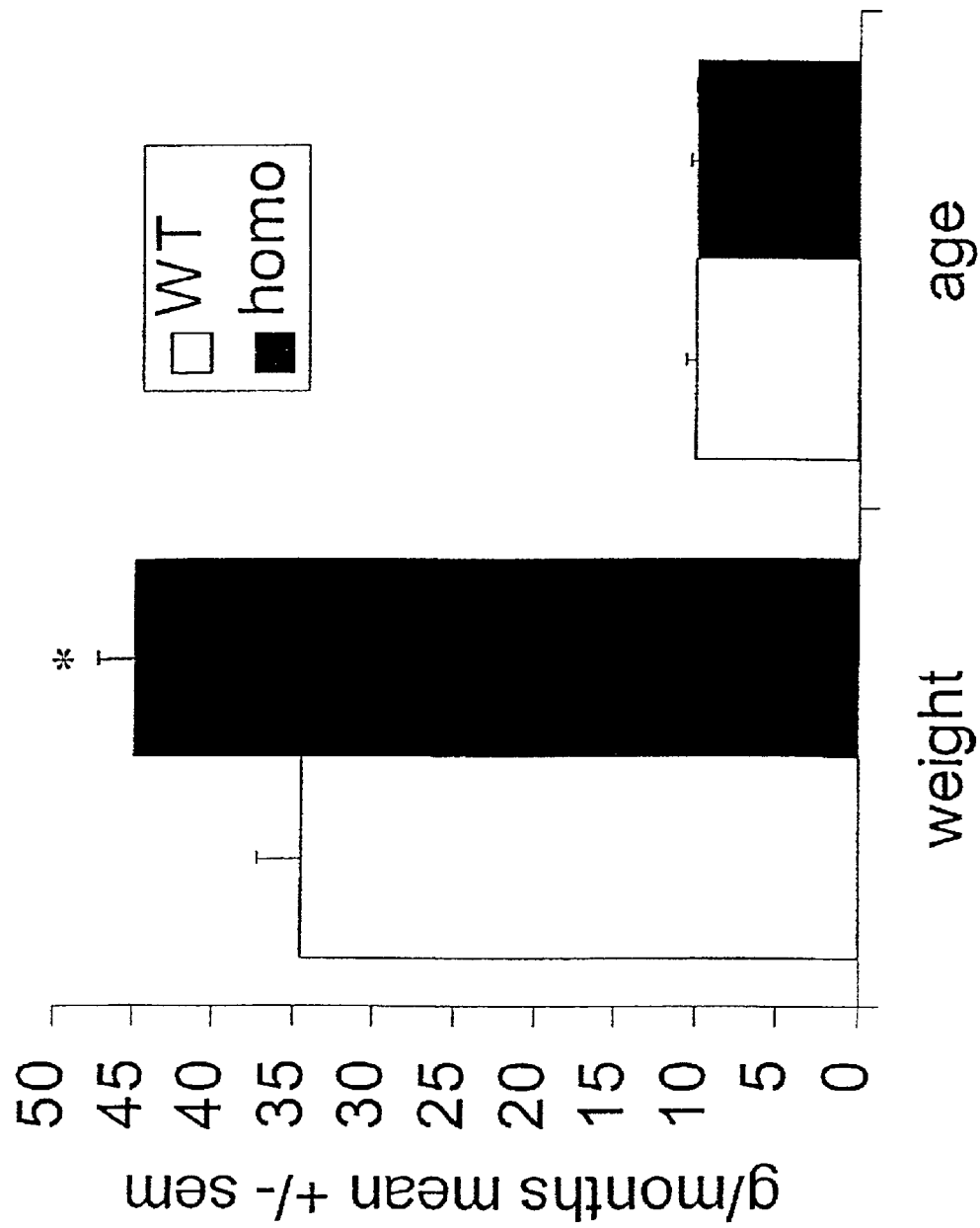

TRANSGENIC MOUSE COMPRISING A DISRUPTION IN AN RGS9 GENE

RELATED APPLICATION DATA

This application claims priority under 35 U.S.C. 119(e) to Ser. No. 60/242,656, filed Oct. 23, 2000, herein incorporated by reference in its entirety.

ACKNOWLEDGEMENT OF GOVERNMENT SUPPORT

This invention was made in part with support under NIH Grant Nos. RO1 AG12288, MH-49176 and GM-29836. The government may have certain rights in this invention.

FIELD OF THE INVENTION

The invention relates generally to regulators of G-protein signaling and more specifically to regulator of G-protein signaling 9 (RGS9) gene knockout animals and methods of using such animals to identify agents that regulate motor or other neurobehaviors. More specifically, the invention relates to methods of modulating dopamine D2 receptor signaling by an RGS protein, such as RGS9.

BACKGROUND

More than 20 mammalian members of the RGS family have been identified many of which are expressed in the brain (Siderovski and Strockbine et al. 1999; Zhang et al. 2000; Simonds and Zhang, 2000). The biological purpose of such multiplicity has remained unclear. These proteins may be involved in functions other than activating GTPase.

Many of the RGS proteins show a region specific expression in rat brain (Gold and Ni et al. 1997). A retina and a brain specific splice variant of RGS9 have been identified (Zhang and Howes et al. 1999). The long form of RGS9 (RGS9–2) is specifically expressed in the striatum (Thomas and Danielson et al. 1998; Rahman and Gold et al. 1999). RGS9 belongs to those members of the RGS family that have a Gγ-like domain and can form a complex with Gβ-proteins, especially Gβ5 (Kovoor, Chen et al. 2000; Simonds and Zhang 2000). This complex seems to be essential for accelerating hydrolysis of Gαt in rod outer segments since mice that do not express both alleles of RGS9 also lack Gβ5 in retina (Chen, Burns et al. 2000).

RGS9 mRNA in striatum was detected in GABAergic medium spiny projection neurons (Thomas, Danielson et al. 1998). Medium spiny neurons in the striatum are believed to give rise to two distinct signaling pathways within the basal ganglia: the direct and the indirect pathway. The latter would originate in neurons that bear dopamine D2 receptors through which dopamine exerts inhibitory mechanisms. The direct pathway would originate in dopamine D1 receptor bearing medium spiny neurons where dopamine acts excitatory. Although this segregation of basal ganglia circuits remains disputed, it very well explains many of the anatomical and pharmacological findings related to dopamine signaling. The inhibitory action of dopamine D2 receptors is without doubt related to coupling to Gαi (Picetti, Saiardi et al. 1997) whereas the excitation mediated via dopamine D1 receptors is coupled through Gαs, Gαo or Gαz (Sidhu 1998)). Therefore it was very unlikely, that RGS9 was linked to dopamine D1 receptor, which interacts with Gαs signaling.

Thus, there is a need for transgenic animals in which RGS9 is not expressed and a need to understand the role of RGS9 in dopamine D2-mediated signaling for modulating complex motor behavior.

SUMMARY OF THE INVENTION

A seminal discovery leading to the present invention is that an RGS protein, more specifically RGS9, modulates dopamine D2-mediated behavior. The present invention provides a transgenic non-human animal having a transgene disrupting or interfering with expression of RGS9, chromosomally integrated into germ cells of the animal and methods of using such transgenic animals to screen agents for modulation of dopamine D2-mediated behavior. The present invention also provides methods of modulating or treating dopamine D2-mediated behavior.

In a particular illustrative example, the invention provides a transgenic mouse including a disruption in the RGS9 gene. The disruption of the RGS9 gene results in an inability of the mouse to produce detectable levels of RGS9.

The invention also provides a method for producing a transgenic mouse exhibiting an inability to produce detectable levels of RGS9. The method includes introducing a transgene into a mouse embryonic stem cell, introducing the stem cell into a mouse embryo, transplanting the embryo into a pseudopregnant mouse and allowing the embryo to develop to term.

A method is also provided for screening a candidate agent for the ability to modulate dopamine D2-mediated behavior in a transgenic animal. The method includes administering to a first transgenic animal a candidate agent and comparing the dopamine D2-mediated behavior of the animal to the dopamine D2-mediated behavior of a second transgenic animal not administered the candidate agent.

A method is also provided for screening a candidate agent for the ability to modulate dopamine D2-mediated behavior. The method includes comparing the interaction between a RGS protein and a dopamine D2 receptor in the presence of a candidate agent and in the absence of a candidate agent, wherein a difference in the interaction between the RGS protein and the dopamine D2 receptor in the presence of the candidate agent compared to the interaction in the absence of the candidate is indicative of a candidate agent that modifies dopamine D2-mediated behavior.

A method is also provided for modulating a level of dopamine D2-mediated behavior. The method includes administering to a subject in need of such treatment an agent, wherein the agent modulates the activity of a RGS protein.

A method is also provided for modulating a locomoter response to a drug. The method includes administering to a subject in need of such treatment an agent, wherein the agent modulates the activity of a RGS protein.

A method is also provided for treating an abnormal motor behavior following a sensitization of dopamine D2 receptors. The method includes administering to a subject in need of such treatment an agent, wherein the agent increases the activity of a RGS protein.

A method is also provided for treating weight gain. The method includes administering to a subject in need of such treatment an agent, wherein the agent increases the activity of a RGS protein.

BRIEF DESCRIPTION OF THE DRAWINGS

FIG. 1A shows the counts per each 5 minute interval of baseline and amphetamine responses (5 m mg/kg; w~t: n=17; homo: n=20). FIG. 1B, 1C, and 1D display the mean counts per 5 of baseline or drug response. Data obtained during minutes 6–30 of each period were calculated. FIG. 1B shows the amphetamine responses. FIG. 1C displays responses to the dopamine D1 agonist SKF38393 (10 mg/kg;wt: n=8; homo: n=10). FIG. 1D shows responses to the dopamine D2 receptor agonist quinpirole (1 mg/kg; wt: n=7; homo: n=10). Al data are displayed as mean +/+SEM.

FIG. 3 shows semiquantitative assessment of involuntary movements (stereotypies and dyskinesia)following chronic treatment with reserpine and an acute challenge with apomorphine (5 mg/kg; mean +/−SEM, wt: n=4; homo: n=7).

FIG. 4 shows the mean weight (g)and mean age (months) of male wild type (n=5)and homozygous RGS knock-out (n=12)mice.

DETAILED DESCRIPTION OF THE INVENTION

Figure 1:
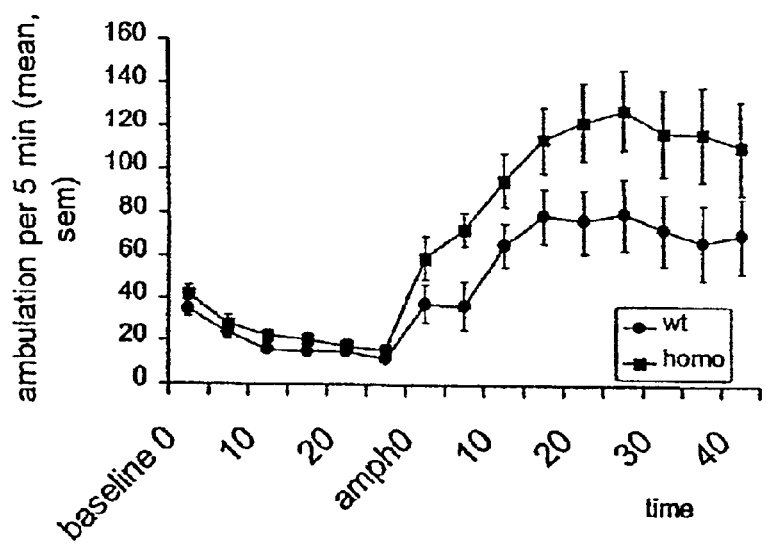
FIGS. 1A to 1D illustrates the locomotion of unlesioned wild type and homozygous RGS9 knock-out mice.
Figure 1:
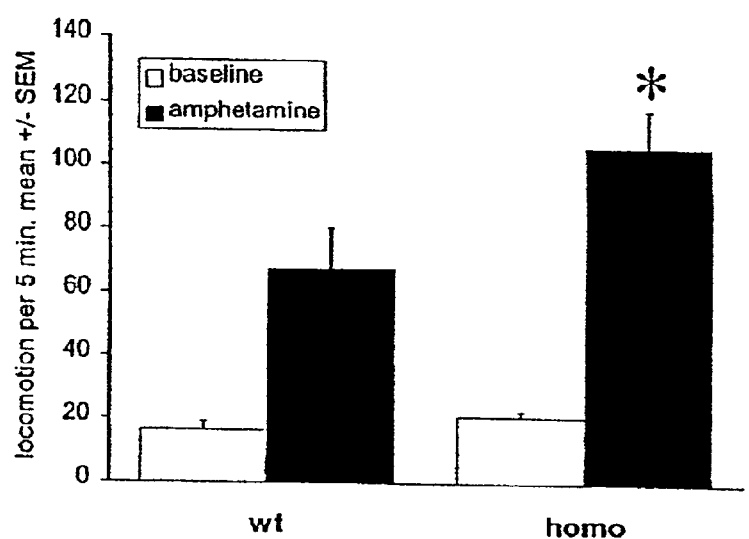
Figure 1:
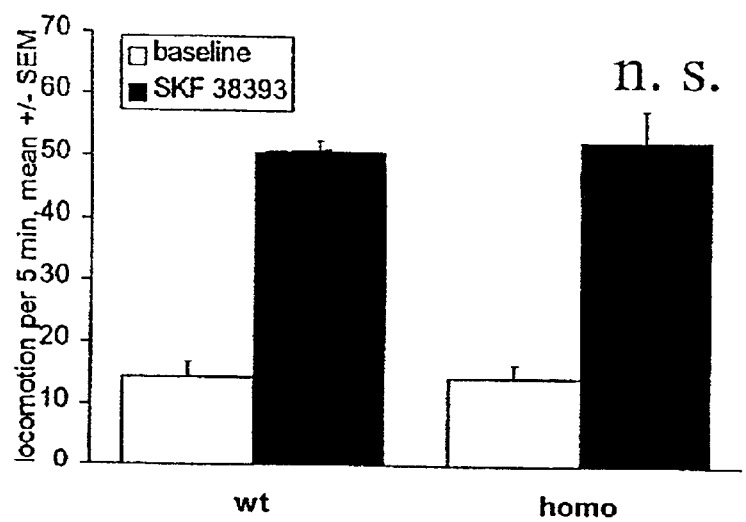
Figure 1:
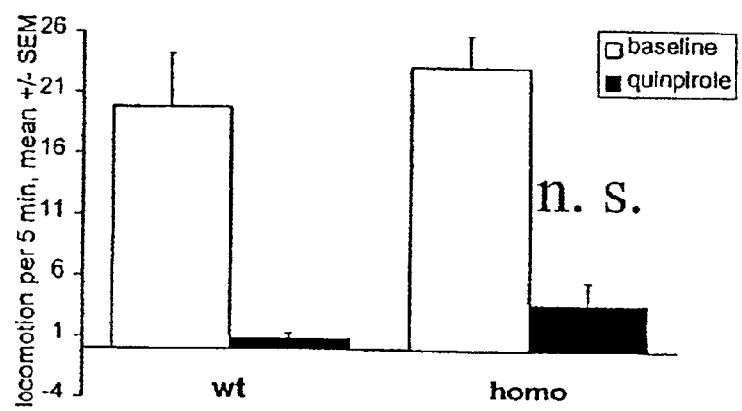

The present invention is based upon the discovery that regulator of G-protein signaling (RGS), more specifically RGS9, modulates dopamine D2-mediated behavior. The present invention provides transgenic RGS deficient animals and methods of using such transgenic animals to screen for candidate agents for modulating dopamine D2-mediated behavior. RGS, more specifically RGS9, can also be used as a drug target for modulating dopamine D2-mediated behavior.

The term "RGS" including any known or unknown proteins that are regulators of G-protein signaling, e.g., RGS family. For example, about 20 mammalian members of the RGS family have been identified. Some RGS proteins show tissue or region specific expression, e.g., in brain. In one embodiment, a RGS protein is RGS9, which includes a retina and a brain specific splice variant of RGS9. In another embodiment, a RGS9 protein is the long form of RGS9 (RGS9–2), which is specifically expressed in the striatum. In still another embodiment, RGS9 belongs to those members of the RGS family that have a Gγ-like domain and can form a complex with Gβ-proteins, especially Gβ5. A RGS protein may also include a portion of a RGS protein that binds or interacts with a dopamine D2 receptor.

In an illustrative example, the transgene to be used in the practice of the subject invention is a DNA sequence comprising a modified RGS9 sequence. In a preferred embodiment, the RGS9 gene is disrupted by homologous targeting in embryonic stem cells. For example, the mature C-terminal region of the RGS9 gene may be deleted. Optionally, the RGS9 disruption or deletion may be accompanied by insertion of or replacement with other DNA sequences, such as a non-functional RGS9 sequence. In other embodiments, the transgene comprises DNA antisense to the coding sequence for RGS9. When appropriate, DNA sequences that encode proteins having RGS9 activity but differ in nucleic acid sequence, e.g., due to the degeneracy of the genetic code or due to mutation, may also be used herein, as may truncated forms, allelic variants and interspecies homologues.

Also included when animals are referred to as transgenic are "knockout animals". For purposes of the subject invention, these animals have been manipulated so that there is disruption or interference with the activity or expression of a gene, i.e., RGS9. As used herein, disruption or interference with the activity or expression refers to a manipulation such that the transgenic animal is irreversibly defective for all or essentially all of an activity of one or more specific gene/allele product(s) relative to the corresponding wild type animal. In a particular embodiment of this type, the knockout animal contains within its genome a specific gene/allele that has been inactivated by a method such as gene targeting. As used herein the term "knockout animal" can therefore include the heterozygote animal (e.g., one defective allele and one wild-type allele), a homozygous animal (e.g., two defective alleles) or an animal having more than one gene having at least allele that has been inactivated. In a particular embodiment of the present invention, a knockout animal is a knockout mouse that has both alleles encoding RGS9 inactivated. A knockout animal that is heterozygous for a particular gene product activity has been manipulated to be defective for all or "essentially all" of the activity of at least one of the particular allele products relative to the corresponding wild type animal.

As used herein a knockout animal or cell defective for "essentially all" of an activity of a specific gene/allele product, is an animal or cell that has less than about 50%, less than about 40%, or less than about 30%, for example, of the gene/allele product activity of the corresponding wild type animal or wild type cell. In a preferred embodiment, the animal or cell has less than or equal to about 20% of the gene/allele product activity of the corresponding wild type animal or wild type cell respectively.

Also provided by the invention is a transgenic mouse comprising a disruption in the regulator of G-protein signaling (RGS9) gene, wherein the disruption of the RGS9 gene results in an inability of the mouse to produce detectable levels of RGS9. RGS9 levels can be detected by methods known to those of skill in the art. For example, Western blotting using antibodies that specifically recognize RGS9 can be used to assess the relative level of RGS9 in tissue samples (see Examples). RGS9 antibodies can also be used in immunocytochemical methods to assess the presence of RGS9 in tissue sections (see Examples). Such antibodies can also be used in antibody-based assays such as radioimmune assays and enzyme-linked immunoabsorbant assays (ELISA) to determine the level of RGS9.

A "transgenic" animal can be produced by cross-breeding two chimeric animals which include exogenous genetic material within cells used in reproduction. Twenty-five percent of the resulting offspring will be transgenic i.e., animals that include the exogenous genetic material within all of their cells in both alleles. Fifty percent of the resulting animals will include the exogenous genetic material within one allele and twenty five percent will include no exogenous genetic material.

Various methods to make the transgenic animals of the subject invention can be employed. The particular method used herein is described in Chen, et al. (2000), Nature 403(6769): 557–60, herein incorporated by reference in its entirety. In addition and generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal.

In another method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191.

In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, Jan. 12, 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention bovine, porcine, ovine and avian animals (e.g., cow, pig, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by crossbreeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y). The viral vector system used to introduce the transgene is typically a replication-defective retro virus carrying the transgene (Jahner, et al., *Proc. Natl. Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., *Nature* 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences that include antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous RGS9 gene(s), a marker gene fragment can be included in the construct in the 3' untranslated region of the transgene and the Northern probe designed to probe for the marker gene fragment. The levels of RGS9 can also be measured in the transgenic animal to establish appropriate expression.

The expression of transgenes can also be assessed by the incorporation of reporter molecules. Reporter molecules, which confer a detectable phenotype on a cell, are well known in the art and include, for example, fluorescent polypeptides such as green fluorescent protein, cyan fluorescent protein, red fluorescent protein, or enhanced forms thereof, an antibiotic resistance polypeptide such as puromycin N-acetyltransferase, hygromycin B phosphotransferase, neomycin (aminoglycoside) phosphotransferase, and the Sh ble gene product; a cell surface protein marker such as the cell surface protein marker neural cell adhesion molecule (N-CAM); an enzyme such as beta-lactamase, chloramphenicol acetyltransferase, adenosine deaminase, aminoglycoside phosphotransferase, dihydrofolate reductase, thymidine kinase, luciferase or xanthine guanine phosphoribosyltransferase polypeptide; or a peptide tag such as a c-myc peptide, a polyhistidine, a FLAG epitope, or any ligand (or cognate receptor), including any peptide epitope (or antibody, or antigen binding fragment thereof, that specifically binds the epitope; see, for example, Hopp et al., *BioTechnology* 6:1204 (1988); U.S. Pat. No. 5,011,912, each of which is incorporated herein by reference). Expression of a reporter molecule can be detected using the appropriate instrumentation or reagent, for example, by detecting fluorescence of a green fluorescent protein or light emission upon addition of luciferin to a luciferase reporter molecule, or by detecting binding of nickel ion to a polypeptide containing a polyhistidine tag. Similarly, expression of a selectable marker such as an antibiotic can be detected by identifying the presence of cells growing under the selective conditions.

A reporter molecule also can provide a means of isolating or selecting a cell expressing the reporter molecule. For example, the reporter molecule can be a polypeptide that is expressed on a cell surface and that contains an operatively linked c-myc epitope; an anti-c-myc epitope antibody can be immobilized on a solid matrix; and cells, some of which express the tagged polypeptide, can be contacted with the matrix under conditions that allow selective binding of the antibody to the epitope. Unbound cells can be removed by washing the matrix, and bound cells, which express the reporter molecule, can be eluted and collected. Methods for detecting such reporter molecules and for isolating the molecules, or cells expressing the molecules, are well known to those in the art (see, for example, Hopp et al., supra, 1988; U.S. Pat. No. 5,011,912). As indicated above, a convenient means of isolating and selecting cells expressing a reporter molecule is provided by using a reporter molecule that confers antibiotic resistance, and isolating cells that grow in the presence of the particular antibiotic.

As used herein, "non-transgenic mouse" refers to a wild-type mouse or a mouse in which the activity or expression of the RGS9 gene has not been manipulated. In such a non-transgenic mouse, the RGS9 level would be expected to be within a normal range. When RGS9 is in the normal range, hydrolysis of fatty acid amides takes place quite rapidly resulting in a low level of fatty acid amides in tissue or in plasma. As used herein, the term "wild type," when used in reference to an animal, for example, a wild type mouse, refers to the animal as it exists in nature.

Also provided by the invention is a method for screening a candidate agent for the ability to modulate dopamine D2-mediated behavior in a transgenic animal. The method includes administering to a first transgenic animal a candidate agent and comparing dopamine D2-mediated behavior of the first transgenic animal to the dopamine D2-mediated behavior of a second transgenic animal not administered the candidate agent. A difference in dopamine D2-mediated behavior in the first transgenic animal administered the candidate agent compared to the second transgenic animal not administered the candidate agent is indicative of a candidate agent that modifies dopamine D2-mediated behavior.

Also provided by the invention is a method for screening a candidate agent, in vitro or in vivo, for the ability to modulate dopamine D2-mediated behavior. The method includes comparing the interaction between a RGS protein and a dopamine D2 receptor in the presence and absence of a candidate agent. A difference in the interaction between the RGS protein and the dopamine D2 receptor in the presence of the candidate agent compared to the interaction in the absence of the candidate agent is indicative of a candidate agent that modifies dopamine D2-mediated behavior.

The interaction between a RGS protein and a dopamine D2 receptor can be any suitable interaction including, without limitation, the quantity, e.g., amount or the strength, e.g., stabilization of the binding between the two proteins. Any suitable methods known to one skilled in the art can be used to determine such interaction.

The term "candidate agent" is used herein to mean any agent that is being examined for ability to modulate dopamine D2-mediated activity in a method of the invention. Although the method generally is used as a screening assay to identify previously unknown molecules that can act as a therapeutic agent, a method of the invention also can be used to confirm that an agent known to have such activity, in fact has the activity, for example, in standardizing the activity of the therapeutic agent.

A candidate agent can be any type of molecule, including, for example, a peptide, a peptidomimetic, a polynucleotide, or a small organic molecule, that one wishes to examine for the ability to act as a therapeutic agent, which is an agent that provides a therapeutic advantage to a subject receiving it. It will be recognized that a method of the invention is readily adaptable to a high throughput format and, therefore, the method is convenient for screening a plurality of test agents either serially or in parallel. The plurality of test agents can be, for example, a library of test agents produced by a combinatorial method library of test agents. Methods for preparing a combinatorial library of molecules that can be tested for therapeutic activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386–390, 1992; Markland et al., *Gene* 109:1319, 1991; each of which is incorporated herein by reference); a peptide library (U.S. Pat. No. 5,264,563, which is incorporated herein by reference); a peptidomimetic library (Blondelle et al., *Trends Anal. Chem.* 14:8392, 1995; a nucleic acid library (O'Connell et al., supra, 1996; Tuerk and Gold, supra, 1990; Gold et al., supra, 1995; each of which is incorporated herein by reference); an oligosaccharide library (York et al., *Carb. Res.*, 285:99128, 1996; Liang et al., *Science,* 274:1520–1522, 1996; Ding et al., *Adv. Expt. Med. Biol.*, 376:261–269, 1995; each of which is incorporated herein by reference); a lipoprotein library (de Kruif et al., *FEBS Lett.*, 399:232–236, 1996, which is incorporated herein by reference); a glycoprotein or glycolipid library (Karaoglu et al., *J. Cell Biol.*, 130:567–577, 1995, which is incorporated herein by reference); or a chemical library containing, for example, drugs or other pharmaceutical agents (Gordon et al., *J. Med. Chem.*, 37:1385–1401, 1994; Ecker and Crooke, *Bio/Technology,* 13:351–360, 1995; each of which is incorporated herein by reference). Accordingly, the present invention also provides a therapeutic agent identified by such a method, for example, a neuroactive therapeutic agent.

Also provided by the invention is a method for modulating a dopamine D2-mediated behavior. The method includes administering to a subject, e.g., human in need of such treatment an effective amount of an agent that either increases or decreases the activity of a RGS protein, especially RGS9. For example, an agent that increases the activity of RGS9 can decrease the level of dopamine D2-mediated behavior, whereas an agent that decreases the activity of RGS9 can increase the level of dopamine D2-mediated behavior.

Dopamine D2-mediated behavior includes any behavior associated with dopamine D2 receptors, through which dopamine exerts inhibitory mechanisms. For example, dopamine D2-mediated behavior includes locomotor behavior, especially locomoter responses to a drug, e.g., amphetamine. Dopamine D2-mediated behavior also includes weight gain and other related behavior. Dopamine D2-mediated behaviors can be assessed by methods know to those of skill in the art and described in Examples.

Also provided by the invention is a method for modulating a locomoter response to a drug, e.g., amphetamine. The method includes administering to a subject, e.g., human in need of such treatment an effective amount of an agent that either increases or decreases the activity of RGS, especially RGS9. For example, an agent that decreases the activity of RGS9 can increase the level of locomotor response.

Also provided by the invention is a method for treating an abnormal motor behavior following a sensitization of dopamine D2 receptors. The method includes administering to a subject, e.g., human in need of such treatment an effective amount of an agent that increases the activity of RGS, especially RGS9. In one embodiment, the sensitization of dopamine D2 receptors is achieved or caused by a drug, e.g., neuroleptics or levodopa. In another embodiment, the abnormal motor behavior is drug induced dyskinesia.

Also provided by the invention is a method for treating weight gain. The method includes administering to a subject in need of such treatment an agent that increases the activity of a RGS protein, e.g., RGS9.

RGS proteins, more specifically RGS9, can also be used as drug targets for Parkinson's disease, drug addition, drug induced dyskinesia, and obesity, for example, using methods as described herein.

The route of administration of an agent or a candidate agent will depend, in part, on the chemical structure of the candidate agent. Peptides and polynucleotides, for example, are not particularly useful when administered orally because they can be degraded in the digestive tract. However, methods for chemically modifying peptides, for example, to render them less susceptible to degradation by endogenous proteases or more absorbable through the alimentary tract are well known (see, for example, Blondelle et al., *Trends Anal. Chem.* 14:83–92, 1995; Ecker and Crooke, *Bio/Technology,* 13:351–360, 1995; each of which is incorporated herein by reference). In addition, a peptide agent can be prepared using D-amino acids, or can contain one or more domains based on peptidomimetics, which are organic molecules that mimic the structure of peptide domain; or based on a peptoid such as a vinylogous peptoid.

An agent or a candidate agent can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the agent or candidate agent can be administered by injection, intubation, orally or topically, the latter of which can be passive, for example, by direct application of an ointment, or active, for example, using a nasal spray or inhalant, in which case one component of the composition is an appropriate propellant.

The total amount of an agent or a candidate agent to be administered in practicing a method of the invention can be administered to a subject as a single dose, either as a bolus or by infusion over a relatively short period of time, or can be administered using a fractionated treatment protocol, in which multiple doses are administered over a prolonged period of time. The agent or candidate agent can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The following examples are intended to illustrate but not limit the invention.

EXAMPLES

The following two strategies were used to investigate the interaction of RGS9 and dopamine D2 receptors.

1. Heterologous expression of RGS9, dopamine D2 receptors in xenopous oocytes, and
2. knockout of RGS9 via mouse genetics.

In addition, immunocytochemistry was performed in wild type mice.

Example 1

Heterologous Expression in Xenopus oocyte cRNA was synthesized in vitro from plasmids containing the cDNA and appropriate promoters for cRNA transcription. Plasmids were linearized prior to cRNA synthesis, and mMESSAGE MACHINE kits (Ambion) were used to generate capped cRNA. The dopamine D2 receptor cDNA was provided by M. Caron (Duke University). The cDNA for the GIRK subunits and mouseRGS9–2 were generated in the inventors' laboratory.

Xenopus oocyte preparation was described previously (Quick, Naeve et al. 1992). cRNA was injected into oocytes at a volume of 50 nl/oocyte using a Drummond microinjector. Oocytes were maintained in a saline buffer (96 mM NaCl, 2 mM KCl, 1 mM $MgCl_2$, 1 mM $CaCl_2$, and 5 mM HEPES, pH 7.5) solution supplemented with sodium pyruvate (2.5 mM)and Gentamycin (50 mg/ml).

All oocytes were injected with 0.01 ng of cRNA for the m2-mAChR and 0.02 ng of cRNA each for GIRK1 and GIRK2.200 nM acetylcholine (ACh)was used as the m2-mAChR agonist. Receptor activation was reversed by simultaneous ACh wash-off and perfusion with the m2-mAChR antagonist, atropine (1 mM). A valve system controlled by the data acquisition software, pCLAMP 6 (Axon Instruments), was used to control solution changes and to minimize wash-in and wash-out times. Two-electrode voltage clamp of the oocytes were performed 36–72 h after cRNA injection. Membrane potential was clamped at 280 mV using a Geneclamp 500 amplifier (Axon Instruments) and pCLAMP 6 software. Electrodes were filled with 3 M KCl and had resistances of 0.5–1.5 megaohms. To reveal inward currents through the inwardly rectifying GIRK channels, recordings were per-formed in oocyte saline buffer with elevated (16 mM) KCl concentration (other components: 82 mM NaCl, 1 niM MgC12 ,1 mM CaC12, and 5 mM HEPES, pH 7.5).

Immunocytochemistry

Brains of wild type mice were dissected after perfusion of the animal with 4% paraformaldehyde, postfixed and dehydrated in 20% sucrose over night. Brain sections of 10 pm thickness were cut using a cryostat microtom (Leica). Immunocytochemistry was performed using the polyclonal antibodies directed against RGS9 (Santa Cruz, dilution 1:1000), dopamine D1 receptors (Chemicon, dilution 1:500)or dopamine D2 receptors (Chemicon, 1:500).

Unilateral Dopamine Depletion

Unilateral 6-hydroxydopamine lesions were performed according to standard procedures, described in rats (Schwarz, Kupsch et al. 1996). Animals were sacrificed using C02. The brain was immediately removed, the striatum dissected and frozen in liquid nitrogen. Protein was extracted using standard procedures. We quantified the amount of RGS9 in lesioned and unlesioned striata and controlled for the degree of dopamine depletion via quntification of dopamine transporter protein.

Immunoblots

Proteins were detected by western blotting of 15 mg total retinal proteins. The polyclonal antibodies were: CT-2 15 (anti-Gb5, used at 1: 2,500 dilution); CT-3 17 (anti-RGSP1, 1: 1000)

RGS9-KO Mice

To investigate the functional role of RGS-9 on dopaminergic transmission in the basal ganglia, both alleles of the RGS-9 gene were inactivated by replacing a 5.5~kilobase (kb) genomic fragment containing exons 2 to 4 with a neomycin resistance marker, MC1neopA. The generation of these mice has been described in detail (Chen, Burns et al. 2000). All experimental procedures complied with NIH guidelines as approved by the Institutional Animal Care and Use Committee of the California Institute of Technology.

Locomotor Activity Measurements

RGS9 knockout mice and their wild type littermates were placed in the photobeam cage rack activity system. The photobeam cage rack activity system was made by San Diego Instruments. Single events represent disruption of two distinct light beams 10 cm apart. Before drug administration, animals were allowed to habituate for 30 min. which was scored as baseline activity. All drugs (d-amphetamine, reserpine, Sigma; SKF 38393, Quinpirole, RBI) were dissolved in physiological saline solutions or water and administered in a final concentration that allowed injection of 100 $\mu$l per 20 mg bodyweight. All drugs were injected intraperitoneally. Drug effects were assessed for 30 min. Bodyweight was measured prior to all drug applications.

Dyskinesia Rating

To score for abnormal involuntary movements we adapted a rating scale that was previously used to score drug induced dyskinesia in monkeys (Goulet and Madra, JPET 2000). Both, trunk and limb, dyskinesia and stereotypic behavior were rated-absent (=O), mild (=1), moderate (=or 2) or severe (=3).

Example 2

Effect of RGS9 on Dopamine D2 Receptor Mediated Activation of GIRK Channels in Oocytes When dopamine D2 receptors and GlRK2 channels are heterologously expressed in xenopous oocytes, activation of these receptors causes a time and dose dependent activation of an inward current. Coexpression of RGS9 induces a significant acceleration of the OFF-kinetics as shown previously using other G-protein coupled receptors (Kovoor, Chen et al. 2000).

Example 3

Immunocytochemsitry

Striatal tissue was double labeled with RGS9 and dopamine D2 or RGS9 and dopamine D1 receptor antibodies. Immunoreactiviy for RGS9 was found in virtually all cells that stained for dopamine D2 receptors (A)but not in cells that stained for dopamine D1 receptors (B).

Example 4

Expression of RGS9 in Dopamine Depleted Striata

RGS9 was quantified in unilaterally dopamine depleted animals. Quantitative western blotting showed an increase of RGS9 protein of 20% in the dopamine depleted striatum controlled to the non-lesioned side.

Example 5
Locomotion in Unlesioned Animals

During the 30 min. habituation period there was no difference between wild type and mutant mice. Intraperitoneal injections of amphetamine(5 mg/kg) induced a robust increase in locomotion in wild type and RGS9 deficient animals. Homozygous knock-out animals showed a significantly greater increase in locomotion than wild type animals (FIG. 1, p<0.05, t-test). Heterozygous animals showed similar responses as wild type animals, which were not significantly different from either wild type or homozygous animals.

Injections of the specific dopamine D1 receptor agonist SKF 38393 (10 mg/kg) produced a 2 fold increase in locomotion in all animals without any differences between genotypes (FIG. 1, p=0.7). The dopamine D2 receptor specific agonist quinpirole (1 mg/kg) dramatically reduced locomotion most likely via activation of presynaptic autoreceptors. RGS9 deficient animals showed a trend of being less affected by this drug, which failed to reach statistical significance (FIG. 1, p=0.1).

Locomotion in Dopamine Depleted Animals

Figure 2:
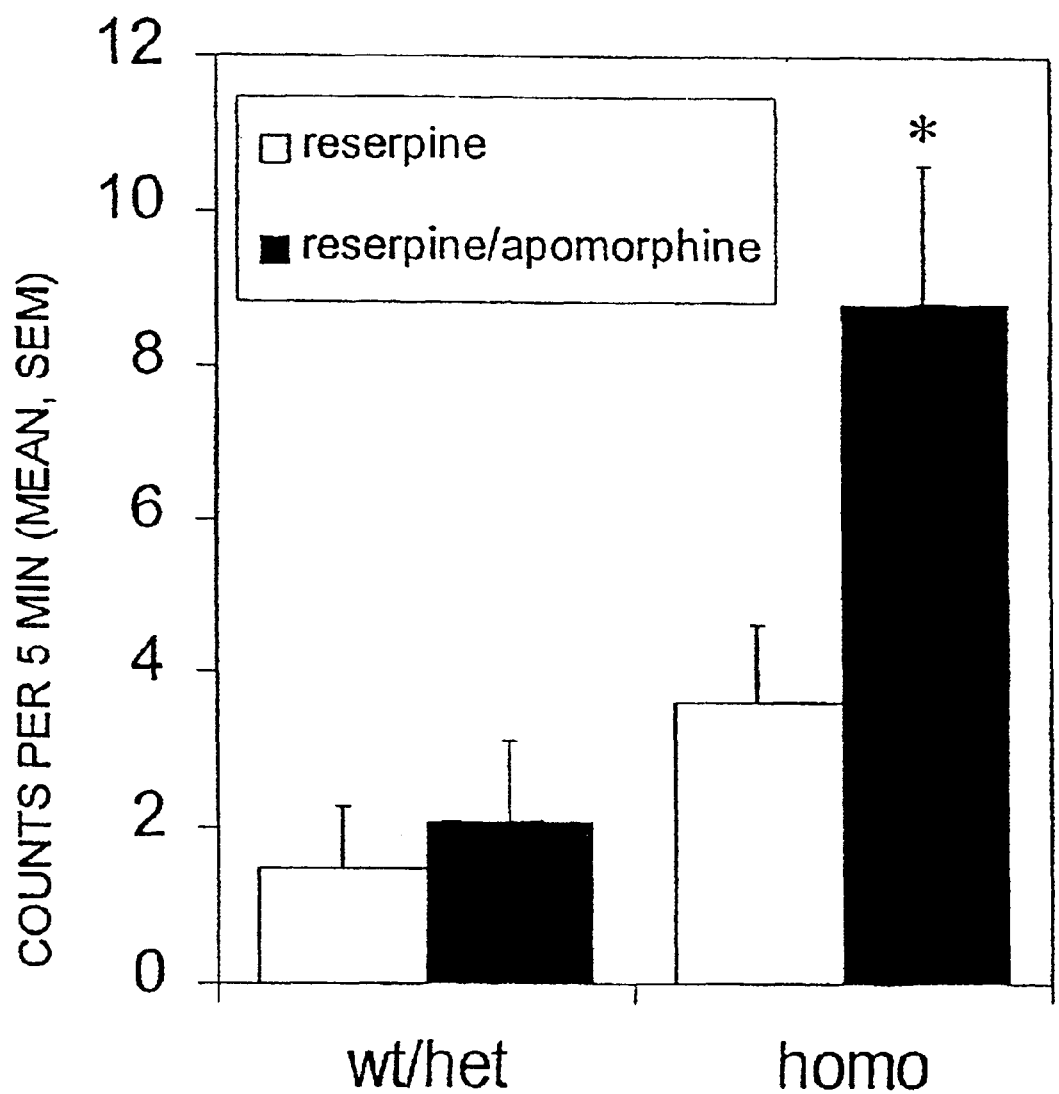
FIG. 2 shows the baseline and apomorphine induced locomotion of reserpine treated animals (mean +/−SEM, wt: n=4; homo: n=7).

There are several options to induce behavioral changes secondary to a dopaminergic deficit in rodents. However, a strong phenotype in mice is difficult o achieve. The most commonly used mouse model (MPTP)does not produce a persisting motor deficit. In mice, unilateral injections of 6-hydroxydopamine do not render robust rotational asymmetry. Therefore, we depleted the animals of dopamine using chronic treatment with reserpine (1 mg/kg per day×5 days). This treatment greatly reduced spontaneous locomotion, Following treatment with reserpine, we assessed locomotor activity induced by the combined dopamine D2 receptor agonist apomorphine (5 mg/kg). Baseline locomotor activity was already greater in homozygous knock-out animals (FIG. 2, n. s.). Apomorphine induced locomotor activity in all animals. However, this effect was more pronounced in homozygous knock out animals (FIG. 2, p<0.05).

In addition, apomorphine induced abnormal motor behavior only in homozygous knockout animals such as dystonia and fat hyperkinetic movements predominantly of the hindlimbs. Using a modified monkey dyskinesia scale, there was a dramatic difference between homozygous knock out animals and wild type or heterozygous mice (FIG. 3).

Example 6

Bodyweight of RGS9 Deficient and Wild Type Mice

Wild type, heterozygous and knock-out littermates were weighed prior to every drug application. FIG. 4 displays the weight of the last cohort of male animals that were used for the reserpine experiments. The mean age in this cohort differed only by one day between wild type (n=5,298 f 19 days) and knock-out (n=12,297±13 days) male animals. There is a significant increase in bodyweight of RGS9 knock-out animals (44.9±2.3 g) compared to wild type (34.6 f 2.7 g, p=0.01, t-test). Heterozygous animals showed a bodyweight of 39±1.5 g (n=10) which was not significantly different from wild types or homozygous mice. The highest weight among wild type or heterozygous animals was 49 g. It may be noteworthy that 5 of the 12 homozygous animals in this cohort displayed a bodyweight of >49 g (50–55 g).

Example 7

This is the first report on a behavioral impact of a single RGS protein outside the retina. Although there seems to be abundance of such proteins, our data stress the specificity of individual members of this family for a given neuronal pathway. In adult mouse and rat brain RGS9 mRNA is predominantly detected in medium-sized spiny neurons in the neostriatum, in neurons of the nucleus accumbens and olfactory tubercle (Thomas, Danielson et al. 1998).

Within the basal ganglia, medium-sized spiny striatal neurons give rise to a direct and indirect pathway. Dopamine excites medium spiny neurons that directly project to the medial segment of the globus pallidus via stimulation of Gas coupled dopamine D1 receptors. Dopamine, on the other hand, inhibits medium spiny neurons that indirectly project to the medial segment of the globus pallidus (via the lateral segment of the globus pallidus and subthalamic nucleus) by activation of Gai coupled dopamine D2 receptors [Picetti, 1997 #17]. Our immunocytochemistry data showing expression of RGS9 only in dopamine D2 receptor bearing medium spiny striatal neurons agrees with the notion that RGS proteins do not affect Gas coupled signal transduction (De Vries, Zheng et al. 2000). Other members of the RGS family are also expressed in suriatum (e. g. RGS2, RGS3, RGS4, RGE5, RGS8, RGS16). An interaction with dopamine receptors has been suggested for RGS2, RGS3 and RGS5 since the mRNA of these members is increased after a single administration of amphetamine (Burchett, Volk et al. 1998). Surprisingly the same study proofed a unique reduction of RGS9 mRNA following amphetamine.

A reduction of RGS9 expression after dopamine overflow following amphetamine administration would match our present data on the increase of RGS9 protein content following unilateral dopamine depletion. However, we were not able to detect any changes in mRNA levels but only increased protein content. The amount of the increase of RGS9 protein was in the same order as the increase of dopamine D2 receptors reported in the same model (&rang and Wamsley 1995). Thus, posttranslational changes may also account for the increase of RGS9 protein in dopamine depleted striata. The primary function of RGS proteins is to accelerate the hydrolysis of GTP and therefore to increase the OFF-kinetics of G-protein signaling (Kovoor, Chen et al. 2000). Since activation of postsynaptic striatal dopamine D2 receptors stimulates motor behavior, lack of RGS9 should enhance while overexpression of RGS9 should decrease locomotion. Our data in RGS9 deficient mice did not show significant differences in baseline behavior indicating that either dopamine D2 mediated signaling is not the major pathway of this type of behavior or that the alteration induced by lack of RGS9 was too small to cause detectable changes. However, the increase of locomotion following treatment with amphetamine in RGS9 knock-out animals is in agreement with prolonged dopamine D2 receptor mediated signaling in these animals.

One may criticize that the overall impact of lack or overexpression of RGS9 on motor behavior is relatively small and in the order of 20 to 50%. However, one also has to keep in mind that the basal ganglia circuitry is highly complex (it seems to get more complex the more we learn about it) and includes many feed-back mechanisms. The amphetamine dose employed in this study produces about a 1000 fold increase of dopamine in the synaptic cleft compared to the physiological tonic dopamine release. The profound response to the rather specific dopamine D1 receptor agonist SKF 38393 in our experiments suggests that the dopamine D1 receptor mediated pathway(s) contribute(s) to at least 50% dopamine stimulated motor behavior in intact mice. Therefore it cannot be expected that an alteration of dopamine D2 receptor mediated signaling can produce effects of more than 50% in dopamine-stimulated behavior.

Having established that RGS9 induces a net decrease in dopamine stimulated locomotion it was surprising to detect the increase of RGS9 protein in dopamine depleted striata. Thus, dopamine depletion may not only induce an increase in dopamine D2 receptors but also an increase in RGS9 protein which diminishes dopamine D2 receptor mediated signaling and therefore may enhance motor consequences induced by dopamine depletion. Since the increase of RGS9 corresponds to the increase of dopamine D2 receptors and there was no evidence for transcriptional changes it indicates that dopamine D2 receptors and RGS9 form rather tight complexes that stabilize RGS9 protein. Our findings of abnormal motor behavior in reserpinized mice that only occurred in mice that lacked RGS9 supports this crucial interaction of dopamine D2 receptors and RGS9.

Little is known about the pathophysiology of drug induced dyskinesia in primates. However, dyskinesia represents a very common problem of treatment with neuroleptics or levodopa. So far, these have not been described in rodents. However, since classical neuroleptics much more block dopamine D2 (like) receptors than any other class of receptors in the brain there is general consensus that these molecules play a prominent role in the pathogenesis of drug induced dyskinesia. Field recordings in non-human primates have shown that the temporal pattern of activity within the basal ganglia is greatly disturbed during such abnormal involuntary movements (Vitek and Giroux 2000). Therefore, it is not so surprising that lack of a protein that contributes to the temporal pattern of dopamine D2 receptor signaling, allows dyskinesia to occur. The fast regulation of RGS9 mRNA following drug application (Burchett, Volk et al. 1998) indicates that dysregulation of RGS9 may contribute to the pathophysiology of drug induced dyskinesia.

In summary, RGS9 plays a crucial role in dopamine D2 mediated motor behavior. RGS9 renders a drug target for treatment of Parkinson's disease, drug-induced behavior or obesity.

REFERENCES

Burchett, S. A., M. L. Volk, et al. (1998). "Regulators of G protein signaling: rapid changes in omRNA abundance in response to amphetamine." J Neurochem 70(5): 2216–9.

Chen, C. K:, M. E. Burns, et al. (2000). "Slowed recovery of rod photoresponse in mice lacking the GTPase accelerating protein RGS9–1." Nature 403(6769): 557–60.

De Vries, L., B. Zheng, et al. (2000). "The regulator of G protein signaling family. Annu" Rev Pharmacol Toxic01 40: 235–71.

Gold, S. J., Y. G. Ni, et al. (1997). "Regulators of G-protein signaling (RGS)proteins: region-specific expression of nine subtypes in rat brain." J Neurosci 17(20): 8024–37.

Kovoor, A., C. K. Chen, et al. (2000). "Co-expression of Gbeta5 enhances the function of two Ggamma subunit-like domain-containing regulators of G protein signaling proteins." J Biol Chem 275(5): 3397–402.

Narang, N. and J. K. Wamsley (1995). "Time dependent changes in DA uptake sites, D1 and D2 receptor binding and mRNA after 6-OHDA lesions of the medial 'forebrain bundle in the rat brain."J Chem Neuroanat 9(1): 41–53.

Picetti, R., A. Saiardi, et al. (1997). "Dopamine D2 receptors in signal transduction and behavior." Crit Rev Neurobiol 11(2–3): 121–42.

Quick, M. W., J. Naeve, et al. (1992). "Incubation with horse serum increases viability and decreases background neurotransmitter uptake in Xenopus oocytes. "Biotechniques 13(3): 357–61.

Rahman, Z., S. J. Gold, et al. (1999). "Cloning and characterization of RGS9–2: a striatalenriched alternatively spliced product of the RGS9 gene." J Neurosci 19(6): 2016–26.

Schwarz, S. C., A. R. Kupsch, et al. (1996). "Cellular immune reactions in brain transplantation: effects of graft pooling and immunosuppression in the 6-hydroxydopamine rat model of Parkinson's disease. GI&" 17(2): 103–20.

Siderovski, D. P., B. Strockbine, et al. (1999). "Whither goest the RGS proteins? 'Crit Rev Biochem Mol Biol34 (4): 2 15–5 1.

Sidhu, A. (1998). "Coupling of D1 and D5 dopamine receptors to multiple G proteins: Implications for understanding the diversity in receptor-G protein coupling. &&" I Neurobiol16(2): 125–34.

Simonds, W. F. and J. H. Zhang (2000). "New dimensions in G protein signalling: G beta 5 and the RGS proteins." Pharm Acta Helv 74(2–3): 333–6.

Thomas, E. A., P. E. Danielson, et al. (1998). "RGS9: a regulator of G-protein signalling with specific expression in rat and mouse striatlim." J Neurosci Res 52(1): 118–24.

Vitek, J. L. and M. Giroux (2000). 'physiology of hypokinetic and hyperkinetic movement disorders: model for dyskinesia." Ann Neurol47(4 Suppl 1): S 13 1–40, Zhang, K., K. A. Howes, et al. (1999). "Structure, alternative splicing, and expression of the human RGS9 gene." Gene 240(1): 23–34.

Although the invention has been described with reference to the above examples, it will be understood that modifications and variations are encompassed within the spirit and scope of the invention. Accordingly, the invention is limited only by the following claims.

What is claimed is:

1. A transgenic mouse whose genome comprises a transgene which disrupts an endogenous regulator of G-protein signaling 9 (RGS9) gene, wherein the disruption of the RGS9 gene results in a lack of detectable RGS9 production, and wherein said mouse exhibits an alteration in dopamine D2-mediated behavior.

2. The transgenic mouse of claim 1, wherein said mouse is homozygous or heterozygous for said disruption of the endogenous RGS9 gene.

3. The transgenic mouse of claim 1, wherein the disruption results from the introduction of a transgene into the genome by homologous recombination with a DNA targeting construct in a mouse embryonic stem cell such that the targeting construct is stably integrated in the genome of the mouse.

4. A method for producing a transgenic mouse exhibiting an inability to produce detectable levels of RGS9, the method comprising:

(a) introducing a transgene comprising a selectable marker sequence into a mouse embryonic stem cell;

(b) introducing said mouse embryonic stem cell into a mouse embryo;

(c) transplanting said embryo into a pseudopregnant mouse;

(d) allowing said embryo to develop to term; and (e) identifying a transgenic mouse whose genome comprises a disruption of the endogenous RGS9 gene, wherein said disruption results in said mouse exhibiting a decreased ability to produce detectable levels of RGS9 as compared to a wild-type mouse.

5. A transgenic mouse produced by the method of claim 4, wherein the genome of the mouse comprises a disruption of the endogenous RGS9, wherein the disruption results in the mouse exhibiting a decreased ability to produce detectable levels of RGS9 as compared to a wild-type mouse.

6. The method of claim 4, wherein the transgenic mouse is homozygous or heterozygous for the disruption of the endogenous RGS9 gene.

7. A method for screening a candidate agent for the ability to modulate dopamine D2-mediated behavior in the transgenic mouse of claim 1 comprising:

(a) administering to a first transgenic mouse of claim 1 a candidate agent; and (b) comparing dopamine D2-mediated behavior of the first transgenic mouse to the dopamine D2-mediated behavior of a second transgenic mouse of claim 1 not administered the candidate agent, wherein a difference in dopamine D2-mediated behavior in the first transgenic mouse administered the candidate agent compared to the second transgenic mouse not administered the candidate agent is indicative of a candidate agent that modifies dopamine D2-mediated behavior.

8. The method of claim 7, wherein the dopamine D2-mediated behavior is motor behavior.

9. The method of claim 7, wherein the dopamine D2-mediated behavior is drug induced behavior.

10. The method of claim 7, wherein the dopamine D2-mediated behavior is weight gain.

* * * * *